US009170236B2

(12) United States Patent
Kessler et al.

(10) Patent No.: US 9,170,236 B2
(45) Date of Patent: Oct. 27, 2015

(54) ACOUSTIC MICRO IMAGING DEVICE WITH A SCAN WHILE LOADING FEATURE

(75) Inventors: Lawrence W. Kessler, Buffalo Grove, IL (US); Michael G. Oravecz, Lombard, IL (US); Thomas Kleinschmidt, Prospect Heights, IL (US); John Billone, Des Plaines, IL (US); Bryan P. Schackmuth, Makati (PH); Joachim Minkwitz, Rockford, IL (US); Igor Komsky, Long Grove, IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 827 days.

(21) Appl. No.: 13/304,125

(22) Filed: Nov. 23, 2011

(65) Prior Publication Data

US 2012/0125110 A1 May 24, 2012

Related U.S. Application Data

(60) Provisional application No. 61/416,610, filed on Nov. 23, 2010.

(51) Int. Cl.
*G01N 29/265* (2006.01)
*G01N 29/06* (2006.01)
*G01N 29/28* (2006.01)

(52) U.S. Cl.
CPC ............ *G01N 29/0681* (2013.01); *G01N 29/28* (2013.01)

(58) Field of Classification Search
USPC .............................. 73/618, 619, 621, 629, 634
See application file for complete search history.

(56) References Cited

U.S. PATENT DOCUMENTS

| 4,021,771 A | 5/1977 | Collins et al. |
| 4,455,872 A | 6/1984 | Kossoff et al. |
| 4,518,992 A | 5/1985 | Kessler et al. |
| 4,768,155 A | 8/1988 | Takishita et al. |
| 4,781,067 A | 11/1988 | Cichanski |
| 4,866,986 A | 9/1989 | Cichanski |
| 4,995,259 A | 2/1991 | Khuri-Yakub et al. |
| 5,351,544 A | 10/1994 | Endo et al. |
| 5,600,068 A | 2/1997 | Kessler et al. |
| 5,602,336 A | 2/1997 | Takeuchi et al. |
| 5,684,252 A | 11/1997 | Kessler et al. |
| 5,714,756 A | 2/1998 | Park et al. |

(Continued)

FOREIGN PATENT DOCUMENTS

| JP | H04-337455 | 11/1992 |
| JP | H06-003455 | 1/1994 |
| JP | 2001-013115 | 1/2001 |

OTHER PUBLICATIONS

U.S. Appl. No. 61/362,131, Inventors Lawrence Kessler, filed Jul. 7, 2010.

(Continued)

*Primary Examiner* — Laura Martin
*Assistant Examiner* — Rose M Miller
(74) *Attorney, Agent, or Firm* — McCracken & Gillen LLC

(57) ABSTRACT

A scanning acoustic microscope comprises a structure including a loading portion and a scanning portion, a transducer disposed in the scanning portion and operable to develop ultrasonic energy, and a controller. A driver is responsive to the controller and is capable of moving the transducer along a scan path with respect to a first plurality of parts disposed in the scanning portion as a second plurality of parts are being loaded into the loading portion.

44 Claims, 9 Drawing Sheets

(56) References Cited

U.S. PATENT DOCUMENTS

| | | |
|---|---|---|
| 6,357,136 B1 | 3/2002 | Erickson et al. |
| 6,460,414 B1 | 10/2002 | Erickson et al. |
| 6,880,387 B2 | 4/2005 | Kessler et al. |
| 6,890,302 B2 | 5/2005 | Oravecz et al. |
| 6,895,820 B2 | 5/2005 | Oravecz et al. |
| 6,912,908 B2 | 7/2005 | Kessler et al. |
| 6,981,417 B1 | 1/2006 | Oravecz |
| 7,000,475 B2 | 2/2006 | Oravecz et al. |
| 7,104,132 B2 | 9/2006 | Mueller |
| 7,395,713 B2 | 7/2008 | Kessler et al. |
| 7,522,780 B2 | 4/2009 | Oravecz et al. |
| 7,530,271 B2 | 5/2009 | Busch et al. |
| 7,584,664 B2 | 9/2009 | Kessler |
| 8,794,072 B2 | 8/2014 | Kessler et al. |
| 2004/0173024 A1 | 9/2004 | McKeon |
| 2004/0200284 A1* | 10/2004 | Kessler et al. ............ 73/603 |
| 2007/0012115 A1 | 1/2007 | Busch et al. |
| 2007/0053795 A1* | 3/2007 | Laugharn et al. ......... 422/99 |
| 2007/0180914 A1 | 8/2007 | Kessler |
| 2009/0095086 A1 | 4/2009 | Kessler et al. |
| 2009/0180931 A1 | 7/2009 | Silbert et al. |
| 2012/0125109 A1 | 5/2012 | Kessler et al. |

OTHER PUBLICATIONS

International Search Report and Written Opinion of the International Searching Authority, Application No. PCT/US11/62116, dated Mar. 26, 2012, (11 pages).

International Search Report and Written Opinion of the International Searching Authority, Application No. PCT/US2011/062101, dated Mar. 19, 2012 (8 pages).

Notice of Reasons for Rejection dated Jun. 10, 2014, for JP Application No. 2013-541057, with English translation attached, Applicant, Sonoscan, (5 pages).

Notice of Reasons for Rejection dated Dec. 2, 2014, for JP Application No. 2013-541057, with English translation attached, Applicant, Sonoscan, (5 pages).

* cited by examiner

Fig. 3B
Fig. 3C
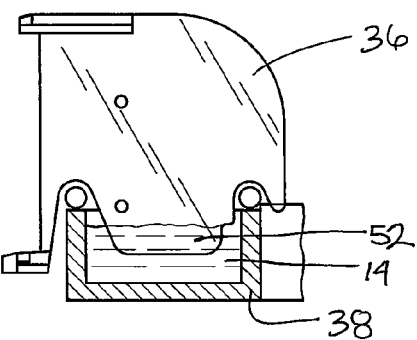
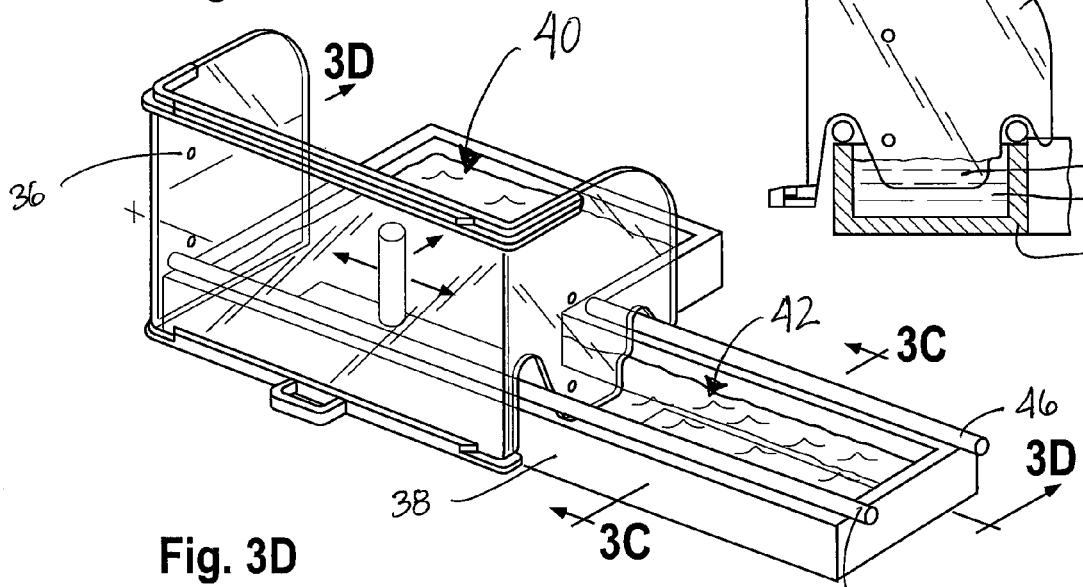
Fig. 3D
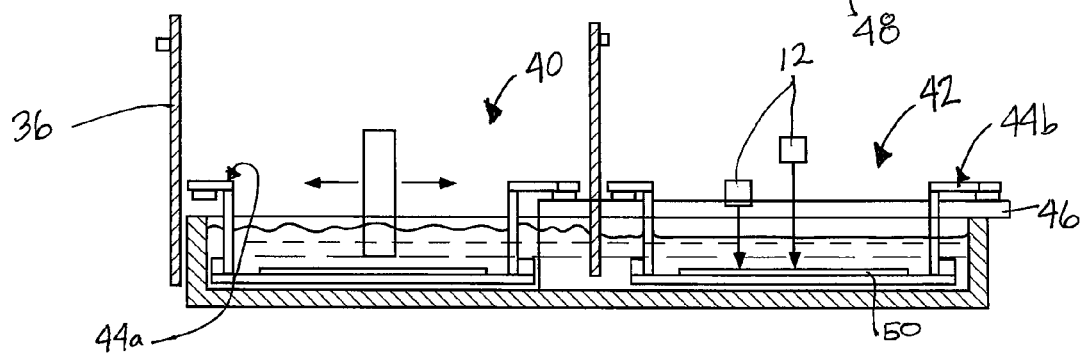
Fig. 3E
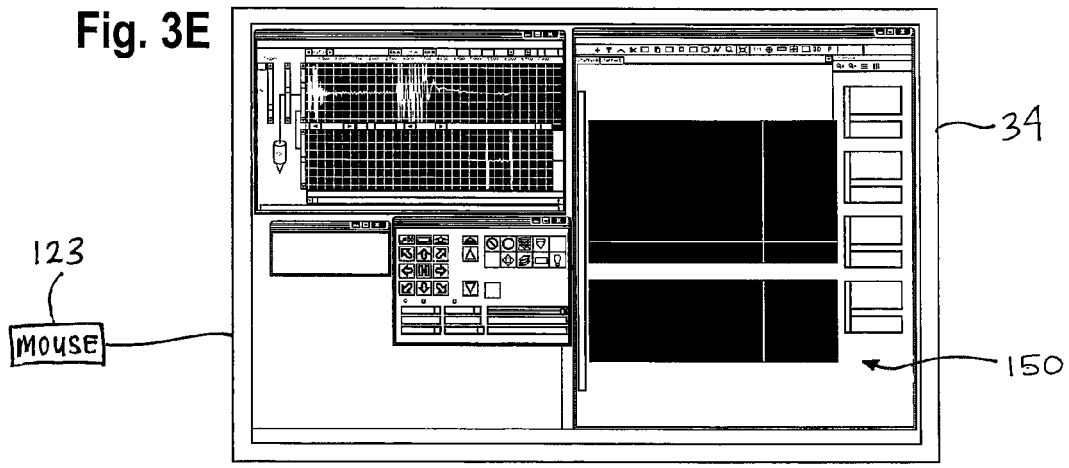

ACOUSTIC MICRO IMAGING DEVICE WITH A SCAN WHILE LOADING FEATURE

CROSS REFERENCE TO RELATED APPLICATIONS

This application claims the benefit of U.S. Provisional Patent Application No. 60/416,610, filed Nov. 23, 2010, which is hereby incorporated by reference herein in its entirety.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to a micro imaging device for inspecting a part with a scan while loading feature.

2. Description of the Background of the Invention

U.S. Pat. No. 7,584,664 is entitled "acoustic micro imaging device having at least one balanced linear motor assembly." U.S. Pat. No. 7,522,780 is entitled "frequency domain processing of scanning acoustic imaging signals." U.S. Pat. No. 7,395,713 is entitled "tray-fed scanning microscope system and method primarily for immobilizing parts during inspection." U.S. Pat. No. 7,000,475 is entitled "acoustic micro imaging method and apparatus for capturing 4D acoustic reflection virtual samples." U.S. Pat. No. 6,981,417 is entitled "scanning acoustic micro imaging method and apparatus for non-rectangular bounded files." U.S. Pat. No. 6,895,820 is entitled "acoustic micro imaging method and apparatus for capturing 4D acoustic reflection virtual samples." U.S. Pat. No. 6,890,302 is entitled "frequency domain processing of scanning acoustic imaging signals." U.S. Pat. No. 6,880,387 is entitled "acoustic micro imaging method providing improved information derivation and visualization." U.S. Pat. No. 6,460,414 is entitled "automated acoustic micro imaging system and method." U.S. Pat. No. 6,357,136 is entitled "scanning acoustic microscope system and method for handling small parts." U.S. Pat. No. 5,684,252 is entitled "method and apparatus for ultrasonic inspection of electronic components." U.S. Pat. No. 5,600,068 is entitled "controlled-immersion inspection." U.S. Pat. No. 4,866,986 is entitled "method and system for dual phase scanning acoustic microscopy." U.S. Pat. No. 4,781,067 is entitled "balanced scanning mechanism." U.S. Pat. No. 4,518,992 is entitled "acoustic imaging system and method." The contents of all of these patents are incorporated by reference into this application as if fully set forth herein.

US Patent Pub. No 20090095086 is entitled "Scanning Acoustic Microscope With Profilometer Function." The content of all of this publication is incorporated by reference into this application as if fully set forth herein.

For more than one year prior to the filing date of this provisional application, the assignee of this application is currently selling a product called Fast Automated C-SAM® Tray Scanning System ("Facts$^2$") and a product called Gen5™ C-Mode Scanning Acoustic Microscope. The promotional materials available on www.sonoscan.com for both of these products, as well as the operation, service and/or maintenance manuals for both products are incorporated by reference into this application as if fully set forth herein.

SUMMARY OF THE INVENTION

According to one aspect of the present invention, a scanning acoustic microscope comprises a transducer, a memory, and a processor. A driver is responsive to the memory and the processor and is adapted to move the transducer in a predetermined path with respect to a tray of parts disposed in a scanning area. A safety enclosure is movable from an open position permitting access to the scanning area to a closed position at least partially enclosing the scanning area. The safety enclosure is adapted when in the closed position to prevent interference with the transducer as the driver rapidly moves the transducer in the predetermined path thereby to minimize a possibility of user injury and allow a tray of parts to be loaded while another is being scanned.

According to another aspect of the present invention, a scanning acoustic microscope includes a transducer operable to develop ultrasonic energy, a controller, and means responsive to the controller for moving the transducer along a scan path with respect to a plurality of parts disposed in a scanning area. A safety enclosure is movable between an open position permitting access to the scanning area and a closed position enclosing the scanning area. The safety enclosure is adapted when in the closed position to prevent user contact with the transducer as the moving means moves the transducer along the scan path and allow a tray of parts to be loaded while another is being scanned.

According to a still further aspect of the present invention, a scanning acoustic microscope comprises a structure including a loading portion and a scanning portion, a transducer disposed in the scanning portion and operable to develop ultrasonic energy, and a controller. A driver is responsive to the controller and is capable of moving the transducer along a scan path with respect to a first plurality of parts disposed in the scanning portion as a second plurality of parts are being loaded into the loading portion.

BRIEF DESCRIPTION OF THE DRAWINGS

Various examples objects, features and attendant advantages of the present invention will become fully appreciated as the same becomes better understood when considered in conjunction with the accompanying drawings, in which like reference characters designate the same or similar parts throughout the several views, and wherein:

FIG. 3B is a isometric view of a portion of the scanning acoustic microscope of FIG. 1A showing various components;

FIG. 3C is a side elevational view, partly in section, wherein the section is taken generally along the line 3C-3C of FIG. 3B;

FIG. 3D is a cross-sectional view of FIG. 3B taken generally along the line 3D-3D;

FIG. 3E is an elevational view of an example of a graphic user interface and display that can be used in connection with embodiments of the present invention;

DETAILED DESCRIPTION OF THE PREFERRED EMBODIMENTS

Figure 1A:
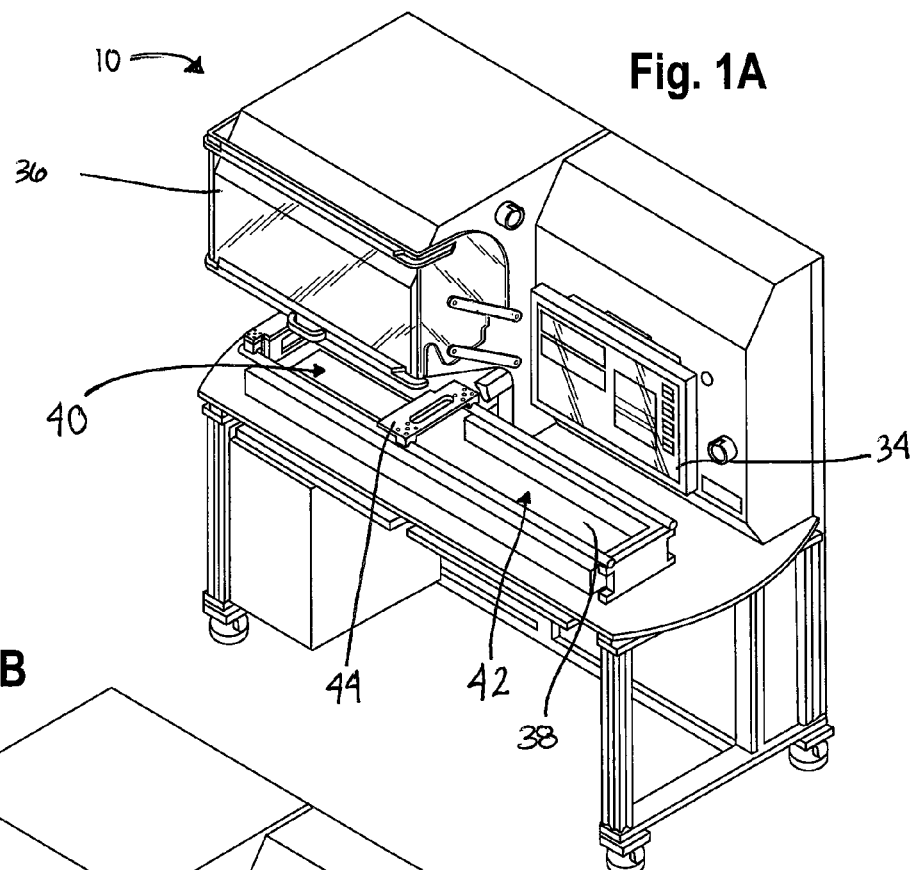
FIG. 1A is an isometric view of a scanning acoustic microscope having a scan while loading feature, wherein the safety door is shown in an upright, open position.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description of the Preferred Embodiments" relates to a requirement of the United States Patent Office, and does not imply, nor should be inferred to limit the subject matter disclosed herein.

In the present disclosure, the words "a" or "an" are to be taken to include both the singular and the plural. Conversely, any reference to plural items shall, where appropriate, include the singular.

Figure 1B:
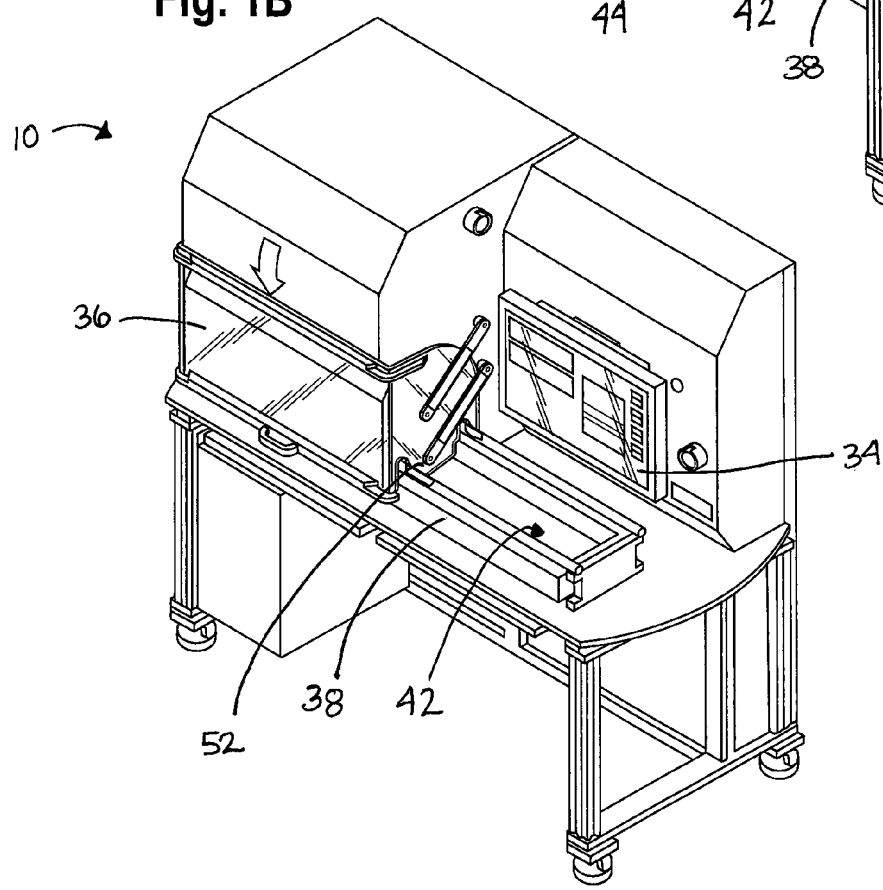
FIG. 1B is an isometric view of the scanning acoustic microscope of FIG. 1A in which the safety door is shown in a closed position.

Referring to FIGS. 1A and 1B, a scanning acoustic microscope 10 having a scan while loading feature is shown. In FIG. 1A, the safety door 36 is shown in an upright, open position. In FIG. 1B, the safety door 36 is shown in a down, closed position with respect to the tank 38. The safety door 36 separates the tank 38 into two portions—a first scanning portion 40 and a second loading portion 42.

Figure 1C:
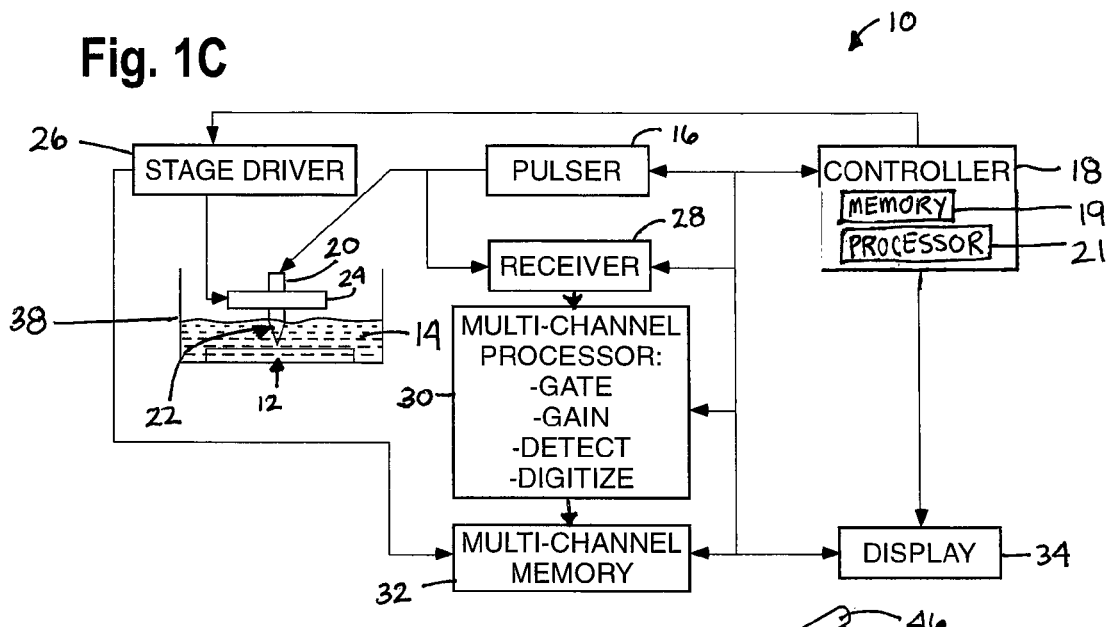
FIG. 1C is a combined diagrammatic view and block diagram of electrical and selected other components of the device of FIGS. 1A and 1B.

Referring to FIG. 1C, the scanning acoustic microscope 10 is adapted to inspect a sample 12 (e.g. an integrated circuit package) that is submerged in a coupling medium or fluid 14, such as water. The sample 12 can be inspected by itself as is the case, for example, in laboratory applications, or can be, for example, mounted on a tray of other parts to be inspected, which typically is the case in commercial applications.

A pulser 16 is under the control of motion controller 18 and is used to excite a transducer 20 to generate pulses of ultrasonic energy 22, typically at frequencies ranging from 10 MHz or lower to 230 MHz or higher. The transducer 20 is scanned in X, Y and Z coordinates by an X-Y-Z stage 24 through an X-Y-Z stage driver 26, which is under the control of controller 18. The X-Y-Z stage driver 26 can include conventional brushless DC motors or, if desired, one or more balanced linear motor assemblies that allow the transducer 20 to be accelerated more quickly than is the case with conventional motors such as brushless DC motors, stepping motors or brush motors.

The controller 18 includes a memory 19 and a processor 21. As described in greater detail hereinafter, instructions are stored in the memory 19 that, when executed by the processor 21, allow a user to generate a scan path of the transducer 20 with respect to a tray of at least one sample(s) 12 that are to be inspected.

The transducer 20 is adapted to receive reflections of the ultrasonic pulses 22 that are directed towards and then reflected by acoustic impedance features present in the sample 12. Such reflection signals are processed by a receiver (not shown) in analog form, and are supplied to a multi-channel processor 30. Digitized versions of the reflection signals can be stored in multi-channel memory 32, and, if desired, shown on display 34 (see FIG. 3E). In a particular embodiment of the present invention, multi-channel memory 32 will store, for example, an in-focus A-scan of a plurality of three dimensionally varied points on the surface of or within the interior of the sample 12, as well as profile measurements which can be used to generate visual depictions on the display 34 of an external profile of each sample 12. This can be useful to determine, for example, whether the sample 12 inspected has warped to any significant degree.

Figure 2A:
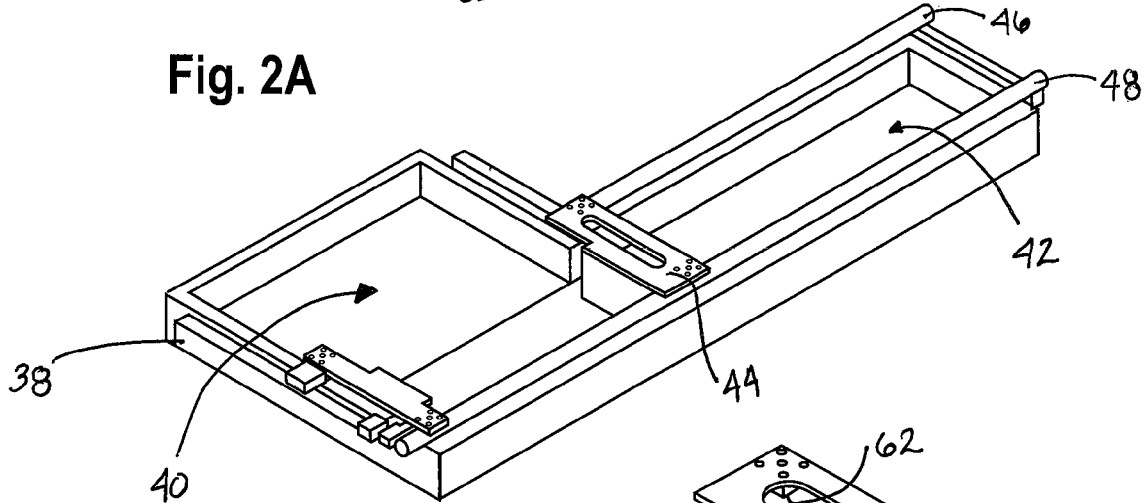
FIG. 2A is an isometric view of the tank shown in FIGS. 1A and 1B.
Figure 3A:
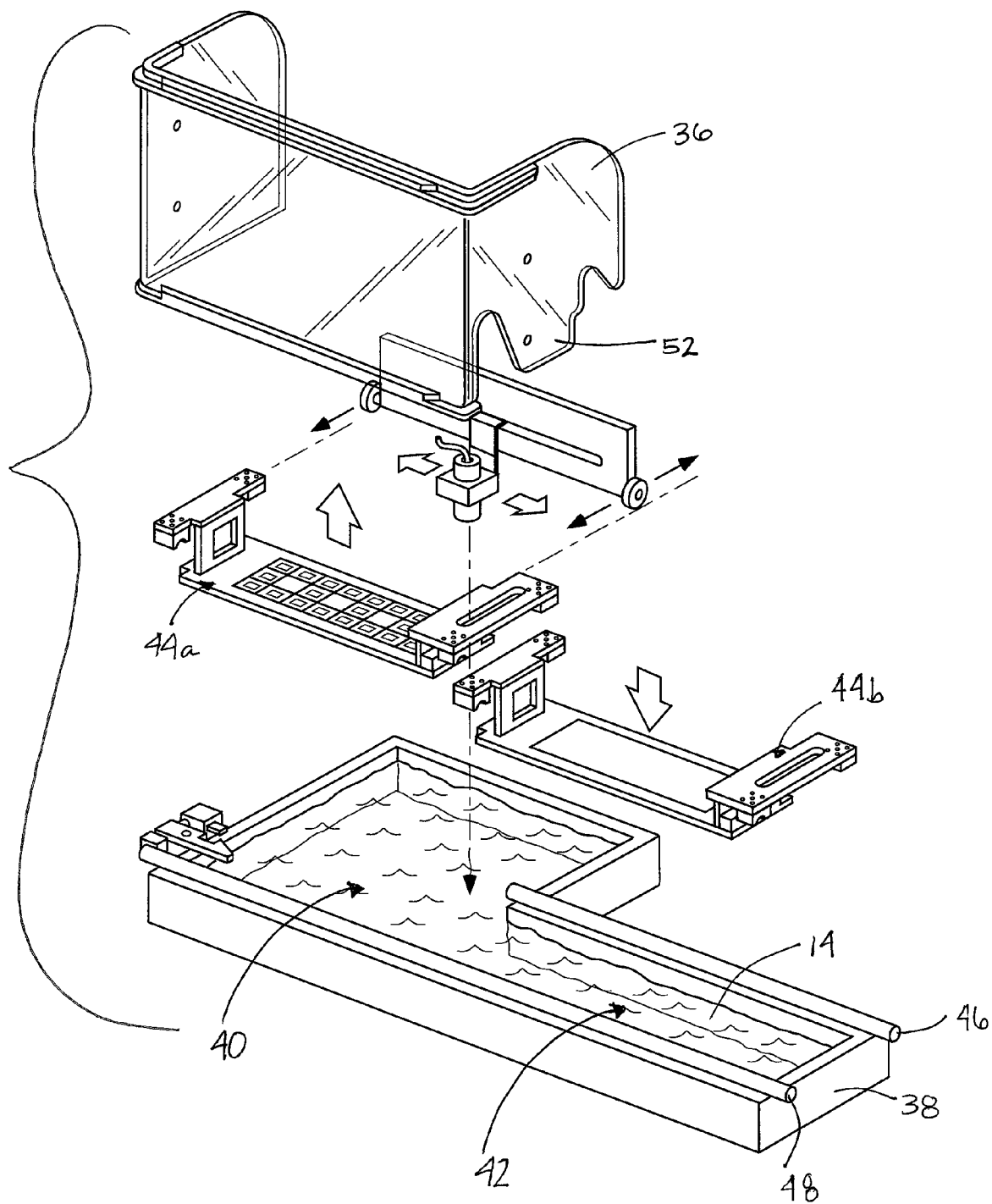
FIG. 3A is an exploded isometric view of a portion of the scanning acoustic microscope of FIG. 1A showing various components.
Figure 7:
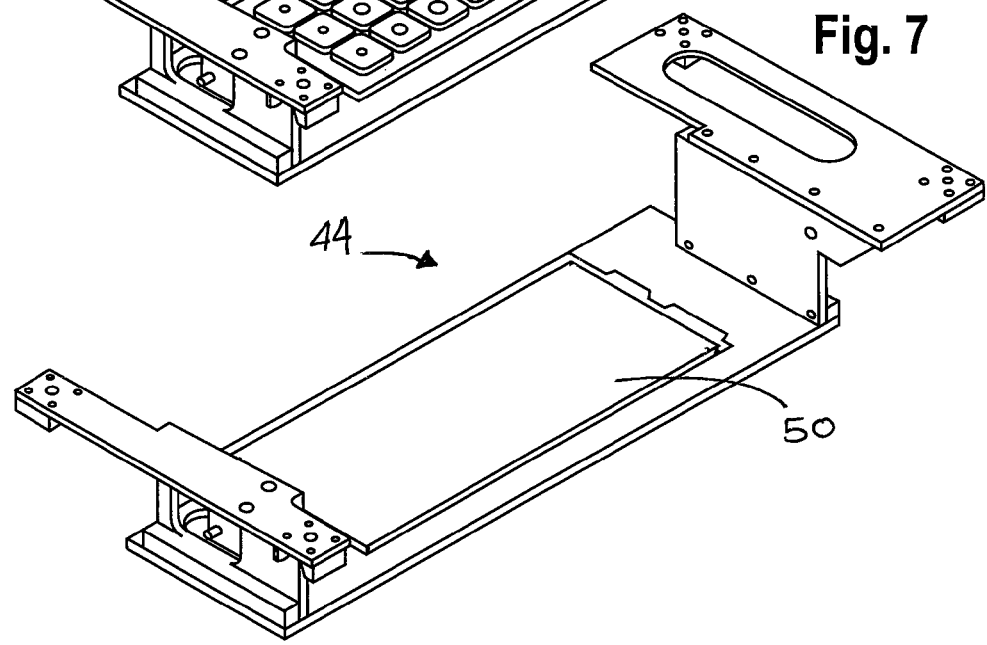
FIG. 7 is an isometric view of a second exemplary embodiment of the fixture that utilizes a glass tray insert on which parts to be inspected are loaded.

FIGS. 2A and 3A show an exemplary tank 38 that has a scanning portion 40 and a loading portion 42. A user is allowed to place a fixture 44 (see FIG. 7) on two rails 46 and 48 so that a parts loading surface 50 is submerged under the coupling fluid 14 contained in both portions 40 and 42 of tank 38. When the fixture 44 is located inside the loading portion 42 of tank 38 outside of the volume enclosed by the safety door 36, the fixture 44 is disposed in a "parts loading" position. Although the loading portion 42 is shown in the drawings as located to the right of the scanning portion 40, the loading portion 42 may be disposed on any side (left, right, front, back) of the scanning portion 40. When the fixture 44 is located in the scanning portion 40 of tank 38 inside of the volume enclosed by the safety door 36, and when the fixture 44 is latched in place, the fixture 44 is located in an insonifying position. This structure allows, for example, the user to brush any bubbles off of the parts to be inspected as they are loaded on the parts loading surface 50, and then to transfer the fixture 44 to the insonifying position without exposing the loaded parts to ambient atmosphere. As readily apparent to one of ordinary skill in the relevant art, the presence of any such bubble on the parts create acoustic impedance features that would disrupt the results of a scan of a part with bubbles.

One advantage of the scanning acoustic microscope 10 is that it allows a user to load a second tray of parts to be inspected at the same time that scanning of a first tray of parts is taking place. As best shown in FIGS. 3A and 3D, a first tray or fixture 44a is loaded into the scanning portion 40 and the safety door 36 is lowered. A second tray or fixture 44b is then placed into the loading portion 42. A user places samples 12 onto the parts loading surface 50 of the second tray 44b and prepares the samples 12 for scanning as discussed above. Once the first tray 44a has been scanned, the safety door is opened and the first tray is removed from the scanning portion 42 by, for example, raising the first tray 44a out of the scanning portion 40 and through the open safety door 36. A third removal portion (not shown) may also be included in the tank 38 or attached thereto. The removal portion may be located in the back, to the left, right, or in front of the scanning portion 40, so that the first tray 44a can be slid from the scanning portion 40 to the removal portion and then lifted from the scanning acoustic microscope 10. Once the first tray 44a is removed from the scanning portion 40, the second tray 44b can be slid from the loading portion 42 into the scanning portion 40 via rails 46 and 48. A third tray or fixture (not shown) can then be loaded into the loading portion 42 and the above process can be repeated.

Figure 11:
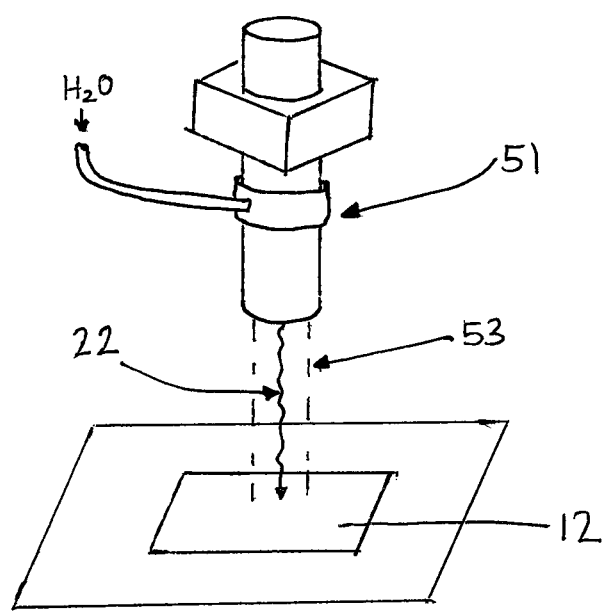
FIG. 11 is an example of a "waterfall" transducer.

In the illustrated embodiment of the present invention, the parts loading surface 50 of the fixture 44 is formed from a solid material such as, for example, glass. In this application, it is possible for through-scanning to take place wherein the transducer 20 includes a receptor located on the under side of the fixture 44 to capture the acoustic energy that passes through the parts to be inspected and the glass surface. In an alternative embodiment of the present invention, the parts loading surface 50 is porous. In this example, it can be formed from a plastic material that is molded to provide a porous parts loading surface 50. In accordance with this alternative embodiment, it is possible to utilize a "waterfall" transducer 51 (as shown in FIG. 11) in which a stream of coupling fluid 53 is emitted towards the sample or parts to be inspected 12, and the ultrasonic pulses 22 are emitted inside the coupling fluid stream 53. The "waterfall" transducer 51 is located above the parts 12 and the water and ultrasonic pulses are directed down toward the parts. It also is possible to apply a vacuum to the underside of the parts through the porous parts loading surface 50 that will minimize the possibility that the parts to be inspected will be dispersed during ultrasonic inspection. In this regard, the memory 19 of the controller 18 includes instructions that, when executed by the processor 21, allow a vacuum to be applied to the underside of the porous parts loading surface 50 for a period of time, the vacuum causing air to be draw into and through the porous parts loading surface 50 to entrain at least some of the flow of coupling fluid that is dispensed onto the parts and to thereby create a pressure that at least partially immobilizes the parts on the parts loading surface 50.

When immersion scanning takes place, the movement of the transducer within the tank of coupling fluid 14 causes "whitecaps" in and agitates the coupling fluid in the tank. In order to reduce the chances that this agitation of coupling fluid could cause parts or chips located on a parts bearing tray to be moved during scanning, a very thin sheet or film can be used that is generally transparent to ultrasonic energy and that has low acoustic impedance. The sheet is placed over the top of the parts bearing tray while it is immersed in the coupling fluid to provide at least some hold down force on the parts as some parts may otherwise float to the surface. Certain plastics are suitable for this purpose, and can be about 5 mils thick. The sheet or film also isolates the parts from the turbulence of the moving transducer(s) thereby holding the parts in place. A clip or clips or the like can be used to further secure the sheet or film on top of the parts.

When through scanning takes place, a transducer is placed below the parts loading surface to capture ultrasonic energy that passes through the parts on the parts loading surface of the tray. If the parts loading surface of a fixture is porous, then an additional sheet or film can be used to minimize the effects of turbulence that are created by the movement of the through scan transducer in the coupling fluid that may agitate the parts on the parts bearing tray by traveling through the porous holes. A clip or clips or the like can be used to further secure the additional sheet or film to the bottom of the parts loading surface.

Referring again to FIG. 1B, the scanning acoustic microscope 10 includes a sensor (not shown) for detecting when the safety door 36 is disposed in the down, closed position. One purpose of the sensor is to allow X-Y-Z motion stage driver 26 to move the transducer 20 only when the safety door 36 is closed. This feature serves to protect the operator of the scanning acoustic microscope 10 from being harmed scanning takes place by, for example, preventing the operator's tie from being caught by the moving transducer 20. The memory 19 of the controller 18 includes instructions that, when executed by the processor 21, prevent the X-Y-Z stage driver 26 from moving the transducer 20 except when a "door closed" signal is sent from the sensor.

As shown in FIGS. 1B, 3A, and 3C, the safety door 36 includes an extension portion 52 that extends down into the tank 38. As previously discussed, the tank 38 contains an amount of coupling fluid 14 through which the transducer 20 is moved in, for example, X-Y raster scans during insonification of the parts loaded on surface 50 (see FIG. 7). Because the transducer 20 can be moved quite quickly during insonification waves and other disturbances in the coupling fluid may be created. One purpose of the extension portion 52 of the safety door 36 is, for example, to minimize the transmission of waves of coupling fluid 14 from the scanning portion 40 of the tank 38 to the second or loading portion 42 of the tank 38. This reduces, for example, the agitation or movement of parts to be inspected as they are loaded on parts loading surface 50.

Figure 2B:
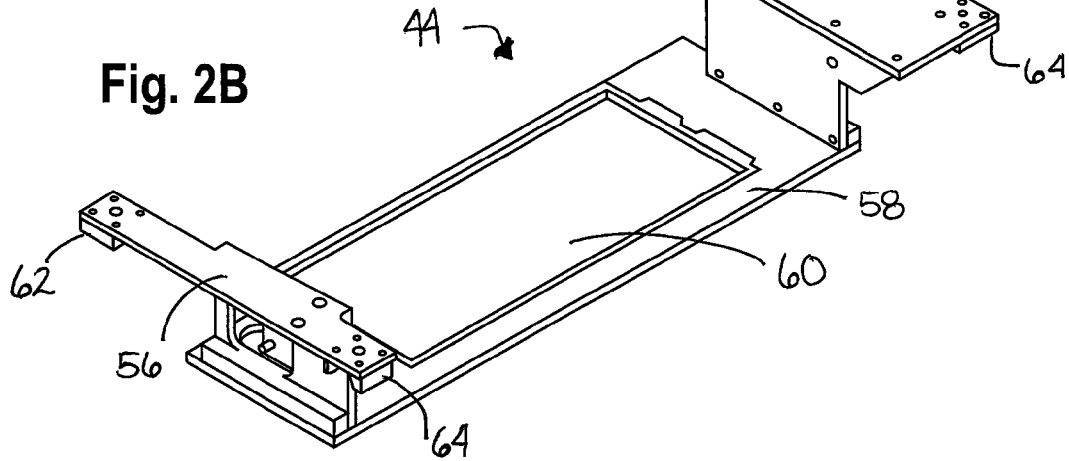
FIG. 2B is an isometric view of the fixture shown in FIGS. 1A and 1B.

FIG. 2B is an isometric view of an exemplary fixture 44 that can be utilized in accordance with embodiments of the present invention. Fixture 44 includes first and second support members 54 and 56 between which a parts support bracket 58 is mounted. Support bracket 58 includes an aperture 60 in which a part bearing tray can be mounted as discussed in greater detail hereinafter.

Figure 4:
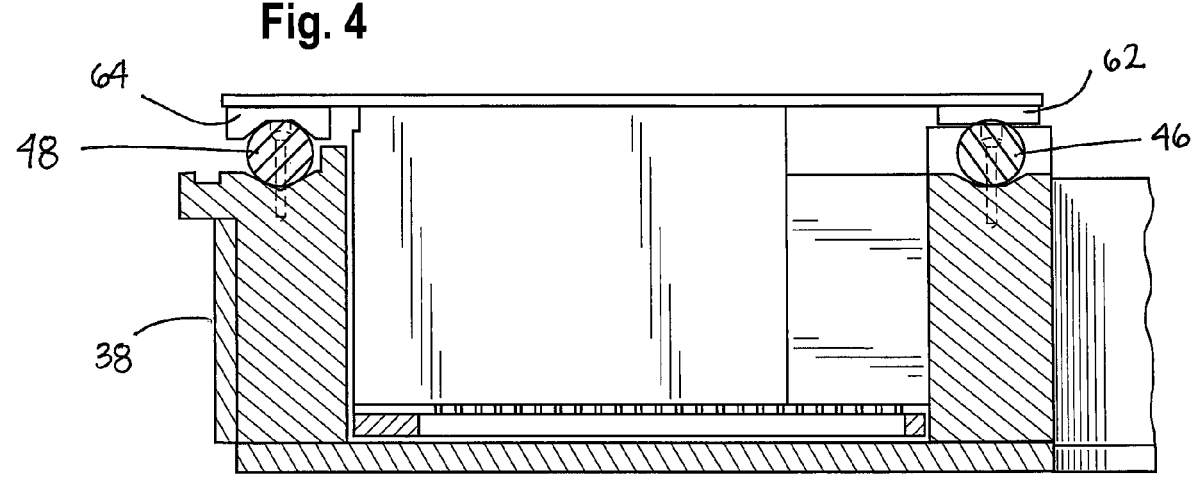
FIG. 4 is a sectional view taken generally along the lines 4-4 of FIG. 3A that shows how the fixture is latched in place with respect to the tank.

Each one of the support members 54 and 56 includes a first bearing 62 and a second bearing 64. The pair of first bearings 62 are adapted to engage rail 46, and the pair of second bearings 64 are adapted to engage rail 48. FIG. 4 is a cross sectional view showing particulars of an exemplary embodiment of the present invention. In this example, the first bearings 62 are flat to engage an upper surface of the rail 46. This prevents the movement of the fixture 44 in a vertical direction perpendicular to the axis of the rail 46. The second bearings 64 are generally U-shaped to capture the rail 48 and thereby prevent movement of the fixture 44 in a direction perpendicular to the axis of the rail 46.

Figure 5:
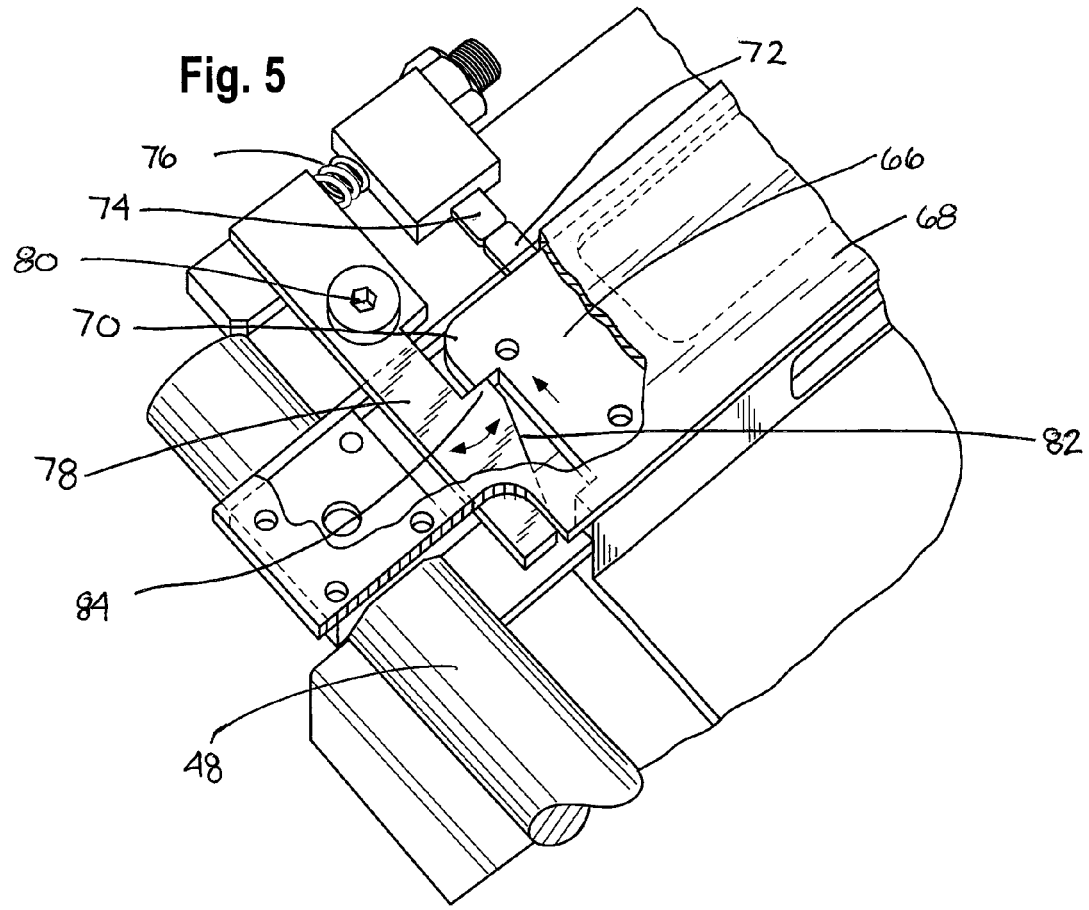
FIG. 5 is a fragmentary isometric view of a portion of the tank that shows how the fixture is latched in place with respect to the tank.

Referring to FIG. 5, a fragmentary isometric view of a portion of the tank 38 and scanning portion 40 is shown which illustrates an exemplary latch that is used to hold the fixture 44 in a calibrated insonifying position. The latch includes an extension member 66 that is, in the illustrated embodiment, integrally formed as a portion of a first support member 68 that is equivalent to first support member 56 shown in FIG. 2B. Extension member 66 includes a shoulder portion 70 and a mating pin 72. When the mating pin 72 is held in contact against abutment pin 74 that is affixed to a part of the scanning portion 40 of the tank 38, the fixture 44 is held in an insonifying position.

A spring 76 biases the pivot member 78 for rotation about axis 80 in a direction towards the extension member 66. The pivot member 78 includes an inclined surface 82 and a shoulder portion 84. As the fixture 44 and first support member 68 are slid along the rails (one of which is shown in FIG. 5 as rail 48) in a direction towards the latch, the inclined surface 82 rides along an outside surface of the shoulder portion 70 of the extension member 66. This compresses the spring 76. One of the engagement surfaces of shoulder portions 70 and 84 is disposed at an angle slightly offset from being perpendicular to the axis of the rail 48 so that, when the pins 72 and 74 touch each other, the bias force applied by the spring 76 ensures that the pivot member 78 does not rotate, unless a user applies enough force to overcome the spring. This latching mechanism, therefore, prevents the fixture 44 from sliding along the rail 48 and, in combination with the engagement of the first and second bearings 62 and 64 with the rails 46 and 48, locks the parts containing the fixture 44 in an insonifying position. This provides a known location that can be used to allow a user to program a path of movement of the transducer 20 with respect to any parts on the parts loading surface 50 of a fixture as discussed in greater detail hereinafter.

Figure 6:
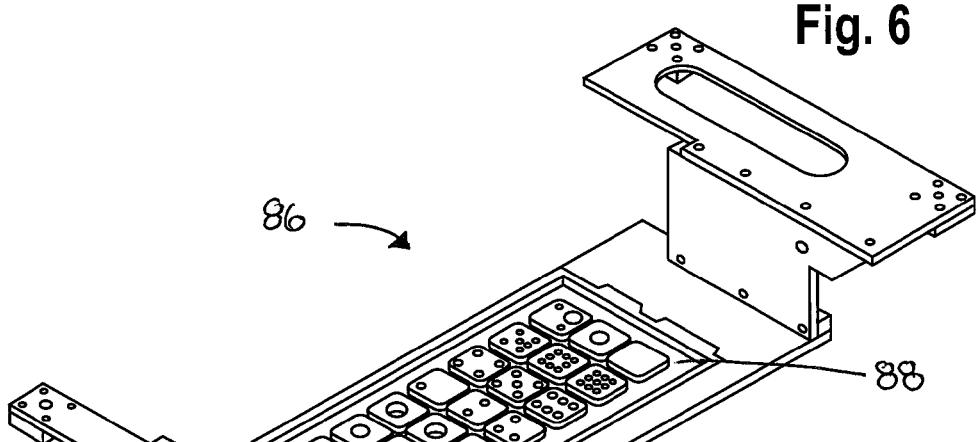
FIG. 6 is an isometric view of a first exemplary embodiment of the fixture that utilizes a plastic tray insert on which parts to be inspected are loaded.

FIG. 6 is an isometric view of an exemplary fixture 86 that is constructed as shown in FIG. 2B, but that includes, for example, a plastic tray 88 inserted in the aperture 60 formed therein. In one embodiment, the plastic tray 88 includes projections (not shown) that are interference fit inside of corresponding apertures 60 formed in the fixture 86. Alternatively, rotatable pins (not shown) inside the fixture 86 can be withdrawn from and then extended to support the plastic tray 88. The tray can be formed from any suitable material (e.g., plastic) and can, in an exemplary application, be formed in a porous manner so that a vacuum can be applied to the underside of the plastic tray 88 to reduce part movement during insonification.

Figure 8A:
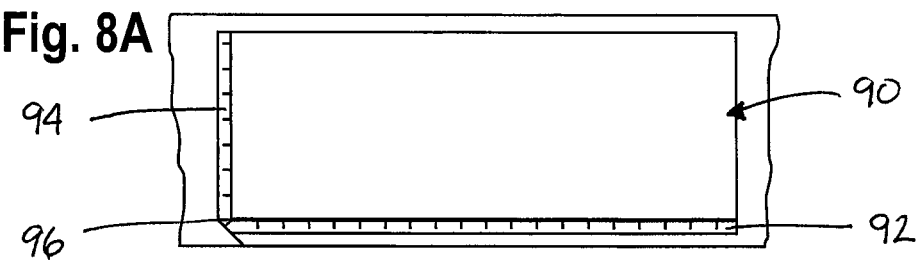
FIG. 8A is a fragmentary plan view of the glass tray shown in FIG. 7.

Referring to FIG. 8, a fragmentary plan view of an alternate embodiment of the present invention is shown. In this example, a parts support tray 90 is formed from a material that is at least generally transparent to ultrasonic energy such as, for example, glass. This embodiment is useful for through scan applications where ultrasonic energy passes through parts and then is read on the opposite side from which the energy originated. The parts support tray 90 is inserted and supported in the aperture 60 formed in a suitable fixture such as fixture 44 shown in FIG. 2B.

The tray 90 includes an x-axis ruler section 92 and a y-axis ruler section 94. When the tray 90 is inserted inside the aperture 60 formed in fixture 44, and when the fixture 44 is fixed in the insonifying position with the pins 72 and 74 held in engagement together by the force of the spring 76, the origin 96 at the junction of the two ruler sections 92 and 94 is held at a known position with respect to the initial, at-rest position of the ultrasonic transducer 20 due to, for example, the construction of the fixture 44. This allows a user to place parts or chips 91 to be inspected on the surface of the tray 90 in columns that are separated by spacer bars. The spacer bars are made of a material heavier than that of the parts 91 and prevent the chips from moving around on the tray once they are placed thereon. In the example shown in FIG. 8B, three columns of parts 98, 100 and 102 are separated by spacer bars 104 and 106. Two parts of the same thickness form column 98, three parts of the same width form column 100, and one part forms column 102.

Figure 8B:
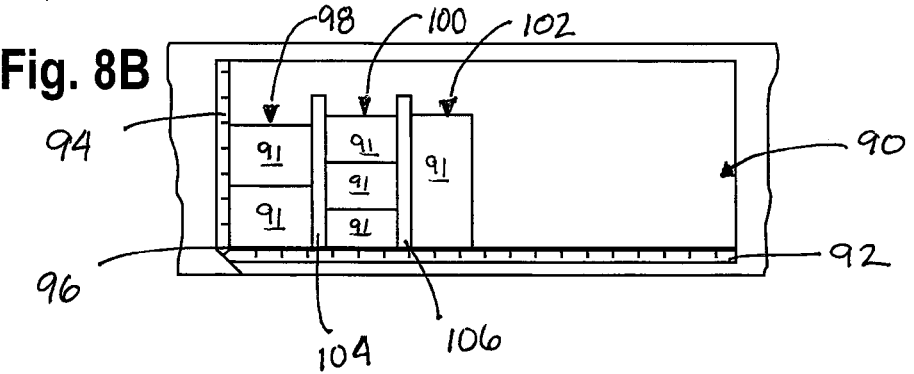
FIG. 8B is a fragmentary plan view of the glass tray of FIGS. 7 and 8A in which a number of samples have been loaded thereon for inspection.
Figure 9A:
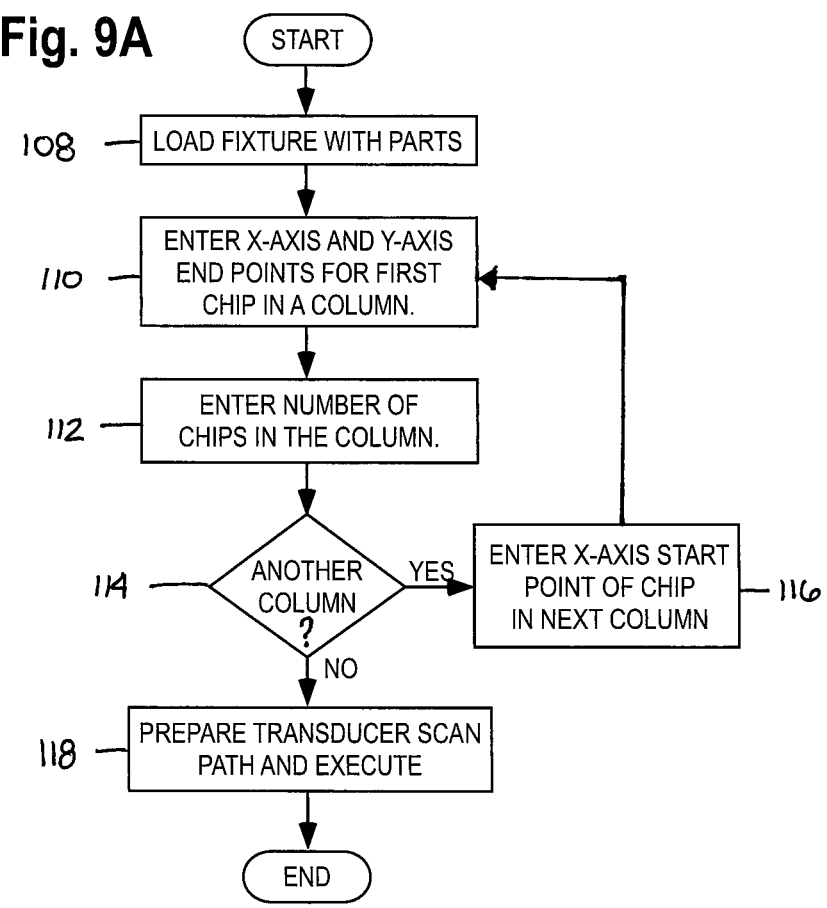
FIG. 9A is a flow chart showing an exemplary process by which a transducer flight path is generated.

FIG. 9A is a flow chart that illustrates process steps by which a user can interact with a graphic user interface on the display 34 (FIGS. 1A-1C) to program a flight path of transducer 20 with respect to a tray of parts such as, for example, tray 90 shown in FIG. 8B. In step 108, a user immerses the fixture 44 in the loading portion 42 of the tank 38, and then places a number of parts or chips 91 to be inspected on the tray 90 held inside the fixture 44 as, for example, shown in FIG. 8B. In step 110, the user interacts with the graphic user interface shown on the display 34 to enter the x-axis and y-axis starting point for the first chip in the first column on the tray 90. In step 112, the user enters the number of chips in the column. If there is another column of parts or chips 91 on the tray 90, step 114, the user enters the x-axis start point of the first chip in that column, step 116. Steps 110 and 112 are repeated for that new row. This process is completed until the dimensions of all of the parts or chips 91 are entered for the total number of columns of parts on the tray 90. Once that is done, step 118, the transducer scan path is computed and then executed so long as the sensor (not shown) indicates that the safety door 36 is in the down, closed position.

Figure 9B:
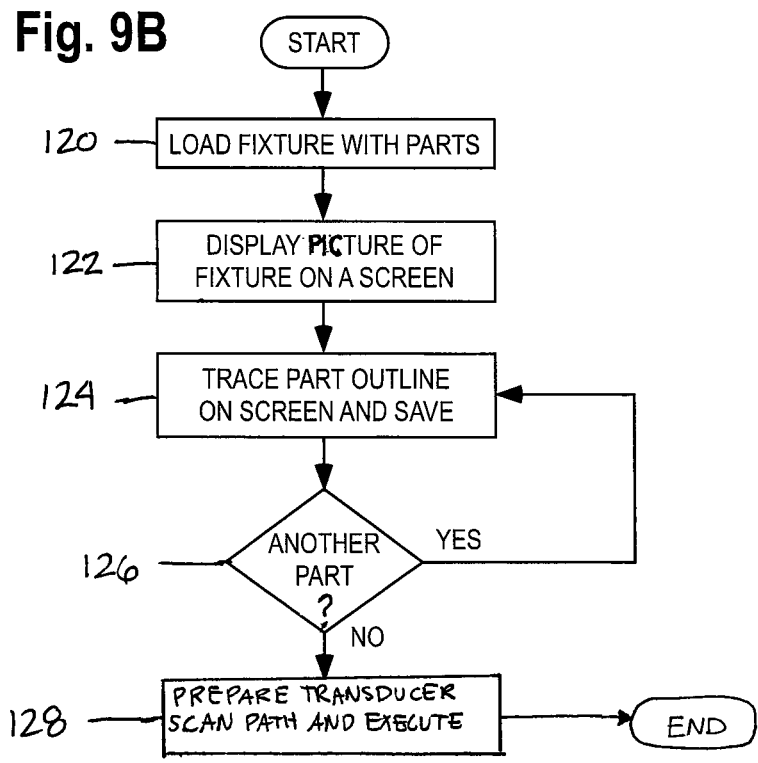
FIG. 9B is a flow chart showing an alternative exemplary process by which a transducer flight path is generated.

FIG. 9B illustrates an exemplary alternative embodiment for allowing a user to program a flight path of the transducer 20 with respect to the parts placed on tray 90. In this embodiment, the tray 90 is loaded with parts or chips 91, step 120, a picture of the tray 90 is taken by a camera (not shown) associated with the scanning acoustic microscope 10, and then the picture is shown on the display 34, step 122. The user then traces the outline of a first one of the parts 91 shown on the display 34 using an appropriate user input device 123 (see FIG. 3E) such as, for example, a mouse or keyboard, step 124. If there is another part on tray 90, step 126, then step 124 is repeated. This process is repeated until the outlines of all parts 91 on tray 90 are traced. When the process is completed, the flight path of the transducer 20 with respect to tray 90 is computed and then executed so long as the sensor (not shown) indicates that the safety door 36 is in the down, closed position.

Other alternatives for programming the flight path of the transducer 20 are within the scope of the invention disclosed and claimed herein. For example, the memory 19 of controller 18 could include a library of parts of known dimensions. In accordance with this alternative exemplary embodiment, the user could enter the part numbers of the parts forming the individual columns on tray 90, together with the x-axis starting points of each column. The flight path could then be programmed by reference to the known dimensions of the parts. Further alternatively, transducer flight paths can be stored in the memory 19 for a given arrangement of parts on the tray 90.

Figure 10:
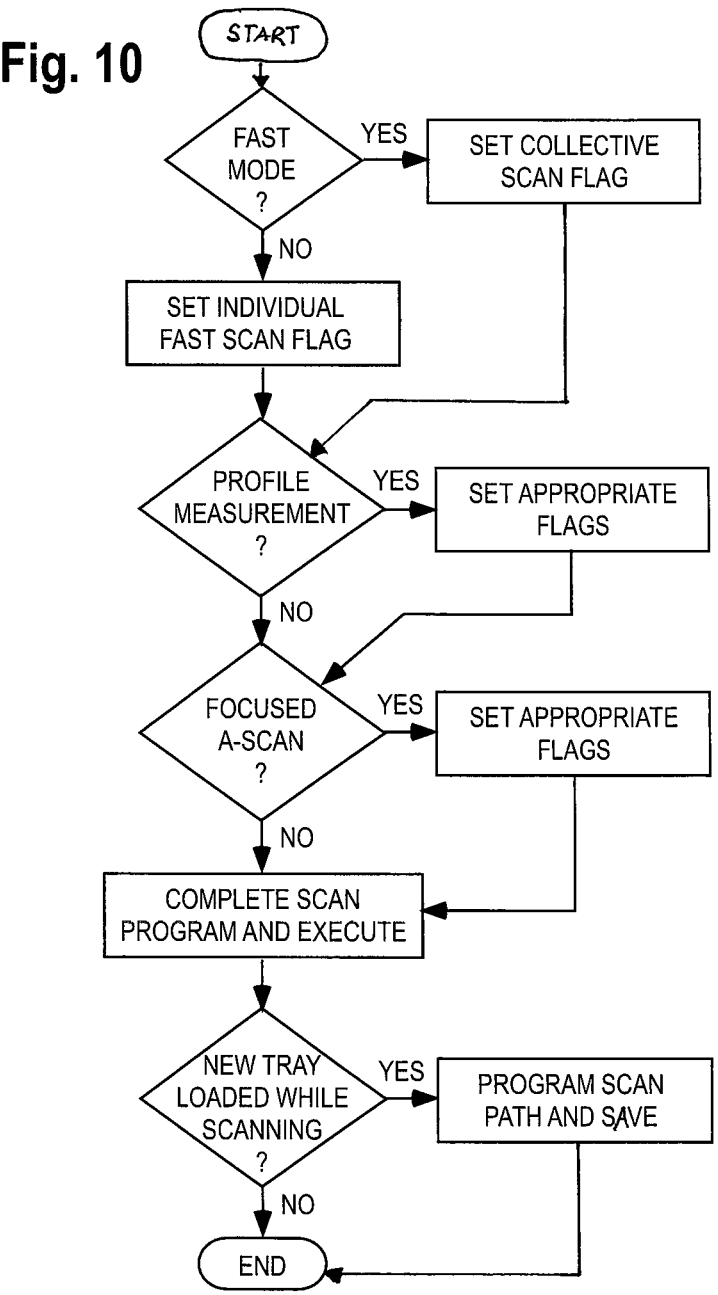
FIG. 10 is a flow chart showing an exemplary process that can be executed after a tray of parts has been loaded but before the scan is executed.

FIG. 10 illustrates a flow chart that allows a user to interact with an appropriate graphic user interface shown on the display 34 to provide additional options available when the tray 90 is scanned. In steps 130 and 132, the user indicates whether a "fast" scanning mode is to be executed for the parts on the tray 90. When "fast" mode is selected, the entire area of the tray 90 that is covered by parts or chips to be inspected is insonified in one x-y raster scan as opposed to having an individual x-y raster scan for each part. A software routine is executed after the scan data is generated to reject and not save data from locations on the tray 90 where no parts are located. The use of the "fast mode" maximizes the time at which transducer 20 is moved at top speed. By utilization of balanced linear motors to cause the transducer 20 to move in the x and y directions of an x-y raster scan, transducer time at top speed is further maximized, thereby further shortening the total scan time. If each part is to be scanned individually, a user indicates that preference by indicating the same in step 134.

In steps 136 and 138, a user indicates a preference to take profile measures of each part located on tray 90. Profile measurements are useful to determine whether or not, for example, each part is warped. The graphic user interface can be programmed to allow profile measurements to be taken for some or all of the parts on tray 90, and to allow internal measurements to be taken as well or not at all with respect to particular parts.

In steps 140 and 142, a user indicates a preference to take focused A-scan measurements at three dimensionally varied points inside of particular ones or all of the parts on the tray 90. In particular, the transducer 20 is used to interrogate each sample on tray 90 at three dimensionally varied locations in the sample. Data developed by the transducer 20 includes for each location interrogated a digitized A-scan for that location. The developed data is stored in a data memory. This allows the creation of a "virtual sample" of acoustic impedance features inside of each sample on tray 90 that can be analyzed at a later time or sent to appropriate personnel at widely dispersed locations.

In step 144, the controller 18 computers the flight path of the transducer 20 with respect to the tray 90, and then executes the same so long as the sensor (not shown) indicates that the safety door 36 is in the down and locked position.

It should be noted that some users of the device disclosed and claimed herein may take action to defeat the action of the sensor that indicates the position of the safety door 36. Such users do this so that they can cause a tray of parts to be inspected with the user is loading a second tray with parts and programming the transducer flight path. It is the applicants' specific intention to try to obtain patent protection on the sale of the machine disclosed and claimed herewith where the sensor has been defeated.

In steps 146 and 148, it is determined if a user has placed a second fixture 44 into the loading portion 42 of the tank 38 while a scanning operation inside of the scanning portion 40 of the tank 38 is taking place. If so, then the user interacts with an appropriate graphic user interface shown on the display 34 to program the transducer flight path while the insonification of the other tray takes place. This allows the operator's time to be more efficiently used to reduce total labor costs for a fixed amount of parts to be inspected. Instead of having an operator wait for a scan to be completed, the operator can, instead, use that previous down time to program the transducer flight path for another tray of parts to be inspected.

One aspect of the present invention is that the memory 19 of the controller 18 contains instructions that, when executed by the processor 21, cause a graphic user interface 150 to be shown on the display (see FIG. 3E), allow a user to enter information about the arrangement of parts that are manually loaded on a parts loading surface of a first fixture that is immersed in a coupling fluid, and computer a flight path of an ultrasonic transducer with respect to the parts on the first fixture, all of which takes place generally simultaneously with the ultrasonic transducer actually being used to inspect parts located on a second fixture immersed in the coupling fluid. These instructions can include, if desired, instructions that, when executed by the processor 21, allow the user to select whether a single x-y raster scan should be taken for all of the parts on the tray. These instructions can include, if desired, instructions that, when executed by the processor 21, allow a user to selectively program for each part whether internal measurements and/or external profile measurements should be made for each part. These instructions can include, if desired, instructions that, when executed by the processor 21, allow A-scans to be taken at three dimensionally varied points inside of one, some or all of the parts to be inspected.

A second aspect of the invention concerns the manner in which a user interacts with the graphic user interface to enter data about the arrangement of parts on the tray. In one embodiment, the user enters information about the x and y axis boundaries of the parts to be inspected that are arranged in columns on the fixture and that are separated by spacer bars. In a second embodiment, the user enters information about the model numbers of the parts to be inspected, with the transducer scan path being calculated by reference to known dimensions of the entered parts that are stored in the memory 19. In a third embodiment, an actual picture of the parts loaded fixture is shown on the display screen, with the user tracing the outline of each part shown on the screen. In a fourth embodiment, a representation of the parts loading surface is shown on the display screen, with the user tracing the outline of each part by means of a cursor or other graphics device.

One advantage of the present invention is that it promotes efficient use of an operator's time. In particular, instead of waiting for the scanning of a particular tray of parts to be completed, the operator can take that time to program the transducer flight path of a second tray of parts. A second advantage of the present invention is that, by utilization of the safety door 36, the area of the scanning acoustic microscope 10 in which the transducer 20 is located can be positioned at the front of the microscope close to the operator. This allows, for example, for easier maintenance of the scanning acoustic microscope 10, and easier replacement of transducers if a different type of scan is to be employed on a next tray. Moreover, there is no requirement that, to remove a tray of parts which already has been inspected, the inspected parts tray must pass above or below another tray that is adapted to be loaded while the other tray is being inspected.

The above-description has been presented with certain features such as the load while scan feature. It is the applicants' intention to preserve the ability to claim a device that includes a load while scan feature in combination with none, any, some or all of the other acoustic microscopy features disclosed in the patents and other information incorporated by reference as if fully set forth herein.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A scanning acoustic microscope, comprising:
 a transducer;
 a memory;
 a processor;
 a structure including a loading portion and a scanning portion, wherein the structure is configured to hold a liquid such that the liquid may flow between the loading portion and the scanning portion;
 a parts loading surface disposed in the loading portion;
 a driver responsive to the memory and the processor that is adapted to move the transducer in a predetermined path with respect to a first plurality of parts disposed in a scanning area of the scanning portion; and
 wherein the structure is configured to allow a second plurality of parts to be loaded in the parts loading surface while the driver moves the transducer along the predetermined path to scan the first plurality of parts.

2. The scanning acoustic microscope of claim 1, wherein the scanning area is disposed in a scanning portion of a tank.

3. The scanning acoustic microscope of claim 2, further including a safety enclosure moveable from an open position permitting access to the scanning area to a closed position at least partially enclosing the scanning area.

4. The scanning acoustic microscope of claim 3, wherein the structure is adapted to hold a coupling fluid.

5. The scanning acoustic microscope of claim 3, wherein the loading portion is disposed on a side of the scanning portion.

6. The scanning acoustic microscope of claim 1, wherein the transducer comprises a waterfall ultrasonic transducer.

7. The scanning acoustic microscope of claim 1, wherein instructions are stored in the memory that, when executed by the processor, permit the predetermined path to be defined by a mouse and shown on a screen that displays representations of the parts to be scanned.

8. The scanning acoustic microscope of claim 1, wherein instructions are stored in the memory that, when executed by the processor, permit the predetermined path to be defined with respect to a tray of parts by a mouse and shown on a screen that displays a photograph of the parts to be scanned.

9. The scanning acoustic microscope of claim 1, wherein instructions are stored in the memory that, when executed by the processor, permit a tray of parts to be scanned in one raster scan.

10. The scanning acoustic microscope of claim 1, wherein instructions are stored in the memory that, when executed by the processor, permit each part of a tray of parts to be individually scanned.

11. The scanning acoustic microscope of claim 1, wherein a scanning area is disposed in the scanning portion of the structure.

12. The scanning acoustic microscope of claim 11, wherein the structure further includes apparatus to transport a tray of parts from the loading portion to the scanning portion.

13. The scanning acoustic microscope of claim 12, wherein the structure includes further apparatus to position a tray of parts at a particular location in the scanning portion.

14. The scanning acoustic microscope of claim 1, further including a sensor and a safety enclosure movable from an open position permitting access to the scanning portion to a closed position at least partially enclosing the scanning portion, wherein the sensor detects an open/closed status of the safety enclosure and wherein the processor is responsive to an output of the sensor to prevent movement of the transducer when the safety enclosure is open.

15. The scanning acoustic microscope of claim 1, further including a sensor and a safety enclosure movable from an open position permitting access to the scanning portion to a closed position at least partially enclosing the scanning portion, wherein the sensor detects an open/closed status of the safety enclosure and wherein the processor is responsive to an output of the sensor to allow movement of the transducer when the safety enclosure is closed.

16. The scanning acoustic microscope of claim 1, in combination with a tray that carries parts to be tested.

17. The scanning acoustic microscope of claim 1, wherein the transducer is positionable in three dimensions and the processor operates the transducer to take focused A-scan measurements in three-dimensionally varied points inside the first plurality of parts.

18. A scanning acoustic microscope, comprising:
a transducer operable to develop ultrasonic energy;
a controller;
a structure including a loading area and a scanning area and wherein the structure is configured to hold a liquid such that the liquid may flow between the loading area and the scanning area;
a parts loading tray disposed in the loading area;
means responsive to the controller for moving the transducer along a scan path with respect to a first plurality of parts disposed in the scanning area; and
wherein the structure is configured to allow a second plurality of parts to be loaded in the parts loading tray while the moving means moves the transducer along the scan path to scan the first plurality of parts.

19. The scanning acoustic microscope of claim 18, further comprising a safety enclosure movable between an open position permitting access to the scanning area and a closed position enclosing the scanning area, wherein the safety enclosure is adapted when in the closed position to prevent user contact with the transducer as the moving means moves the transducer along the scan path and allows a tray of parts to be loaded while another is being scanned.

20. The scanning acoustic microscope of claim 18, wherein the scanning area is adapted to receive the first plurality of parts during a period of time while the second plurality of parts are loaded in the loading area.

21. The scanning acoustic microscope of claim 20, wherein the loading area is disposed on a side of the scanning area.

22. The scanning acoustic microscope of claim 18, wherein the transducer comprises a waterfall ultrasonic transducer.

23. The scanning acoustic microscope of claim 18, wherein instructions are stored in a memory that, when executed by a processor, permit the predetermined path to be defined by a mouse and shown on a screen that displays representations of the parts to be scanned.

24. The scanning acoustic microscope of claim 18, wherein instructions are stored in a memory that, when executed by a processor, permit the predetermined path to be defined with respect to the parts loading tray by a mouse and shown on a screen that displays a photograph of the parts to be scanned.

25. The scanning acoustic microscope of claim 18, further including a sensor and a safety enclosure movable from an open position permitting access to the scanning area to a closed position at least partially enclosing the scanning area, wherein the sensor detects an open/closed status of the safety enclosure and wherein the controller is responsive to an output of the sensor to prevent movement of the transducer when the safety enclosure is open.

26. The scanning acoustic microscope of claim 18, further including a sensor and a safety enclosure movable from an open position permitting access to the scanning area to a closed position at least partially enclosing the scanning area, wherein the sensor detects an open/closed status of the safety enclosure and wherein the controller is responsive to an output of the sensor to allow movement of the transducer when the safety enclosure is closed.

27. The scanning acoustic microscope of claim 18, wherein the transducer is positionable in three dimensions and the controller operates the transducer to take focused A-scan measurements in three-dimensionally varied points inside the first plurality of parts.

28. A scanning acoustic microscope, comprising:
a structure including a loading portion and a scanning portion, wherein the structure is configured to hold a liquid such that the liquid may flow between the loading portion and the scanning portion;
a transducer disposed in the scanning portion and operable to develop ultrasonic energy;
a controller; and a driver responsive to the controller capable of moving the transducer along a scan path with respect to a first plurality of parts disposed in the scanning portion as a second plurality of parts are being loaded into the loading portion.

29. The scanning acoustic microscope of claim 28, wherein the structure further includes a safety enclosure movable between an open position permitting access to the scanning portion and a closed position enclosing the scanning portion.

30. The scanning acoustic microscope of claim 29, wherein the safety enclosure is adapted when in the closed position to prevent user contact with the transducer as the moving means moves the transducer along the scan path and allow a first tray of parts to be loaded into the loading portion while a second tray of parts is being scanned.

31. The scanning acoustic microscope of claim 30, wherein the structure includes apparatus to transport the second tray of parts into the scanning portion after the first tray of parts has been scanned and removed from the scanning portion.

32. The scanning acoustic microscope of claim 31, wherein the structure includes further apparatus to position each tray at a particular location in the scanning portion.

33. The scanning acoustic microscope of claim 32, wherein the structure comprises a tank adapted to hold a coupling fluid.

34. The scanning acoustic microscope of claim 32, wherein the loading portion is disposed on a side of the scanning portion.

35. The scanning acoustic microscope of claim 30, wherein the transducer comprises a waterfall ultrasonic transducer.

36. The scanning acoustic microscope of claim 30, wherein instructions are stored in a memory that, when executed by a processor, permit the scan path to be defined by a mouse and shown on a screen that displays representations of the parts to be scanned.

37. The scanning acoustic microscope of claim 30, wherein instructions are stored in a memory that, when executed by a processor, permit the scan path to be defined with respect to the second tray of parts by a mouse and shown on a screen that displays a photograph of the parts to be scanned.

38. The scanning acoustic microscope of claim 30, wherein instructions are stored in a memory that, when executed by a processor, permit the first tray of parts to be scanned in one raster scan.

39. The scanning acoustic microscope of claim 30, wherein instructions are stored in a memory that, when executed by a processor, permit each part of the first tray of parts to be individually scanned.

40. The scanning acoustic microscope of claim 28, wherein the structure further includes a safety enclosure movable between an open position permitting access to the scanning portion and a closed position enclosing the scanning portion and wherein a sensor detects an open/closed status of the safety enclosure and wherein the controller is responsive to an output of the sensor to prevent movement of the transducer when the safety enclosure is open.

41. The scanning acoustic microscope of claim 28, wherein the structure further includes a safety enclosure movable between an open position permitting access to the scanning portion and a closed position enclosing the scanning portion and wherein a sensor detects an open/closed status of the safety enclosure and wherein the controller is responsive to an output of the sensor to allow movement of the transducer when the safety enclosure is closed.

42. The scanning acoustic microscope of claim 28, in combination with a tray that carries parts to be tested.

43. The scanning acoustic microscope of claim 28, in combination with coupling fluid.

44. The scanning acoustic microscope of claim 28, wherein the transducer is positionable in three dimensions and the transducer is operated to take focused A-scan measurements in three-dimensionally varied points inside the first plurality of parts.

* * * * *